United States Patent [19]

Oliveira et al.

[11] Patent Number: 5,002,151

[45] Date of Patent: Mar. 26, 1991

[54] EAR PIECE HAVING DISPOSABLE, COMPRESSIBLE POLYMERIC FOAM SLEEVE

[75] Inventors: Robert J. Oliveira, Maplewood; Davis W. Chamberlin, St. Paul; Martin P. Babcock, Oakdale, all of Minn.

[73] Assignee: Minnesota Mining and Manufacturing Company, St. Paul, Minn.

[21] Appl. No.: 416,856

[22] Filed: Oct. 4, 1989

Related U.S. Application Data

[63] Continuation-in-part of Ser. No. 938,540, Dec. 5, 1986, Pat. No. 4,880,076.

[51] Int. Cl.$^5$ .............................................. H04R 25/02
[52] U.S. Cl. ................................... 181/130; 181/135; 381/68.6
[58] Field of Search .................. 181/130, 134, 135; 381/68, 68.5, 68.6, 68.7; 128/864

[56] References Cited

U.S. PATENT DOCUMENTS

| Re. 29,487 | 12/1977 | Gardner, Jr. .................. 128/152 |
| 789,876 | 5/1905 | Pape . |
| 1,753,817 | 4/1930 | Aber . |
| 1,830,198 | 11/1931 | French . |
| 2,939,923 | 6/1960 | Henderson . |
| 3,061,689 | 10/1962 | McCarrell et al. . |
| 3,169,600 | 2/1965 | Thomas .................. 181/24 |
| 3,170,046 | 2/1965 | Leale . |
| 3,312,789 | 4/1967 | Lewis et al. . |
| 3,415,246 | 12/1968 | Hill .................. 128/152 |

(List continued on next page.)

FOREIGN PATENT DOCUMENTS

| 0270268 | 12/1987 | European Pat. Off. . |
| 0310866 | 9/1988 | European Pat. Off. . |
| 2818273 | 8/1979 | Fed. Rep. of Germany . |
| 1395197 | 1/1965 | France . |
| 2091063A | 7/1982 | United Kingdom . |
| 2155276A | 9/1985 | United Kingdom . |

OTHER PUBLICATIONS

Killion et al., (1988) "Zwislocki was right...", Hearing Instruments 39(1), 14–18.
Killion (1981) "Earmold Options for Wideband Hearing Aids", Journal of Speech and Hearing Disorders 46(1), 10–20.
Berger (1987) "Can Hearing Aids Provide Hearing Protection?", Hearing Instruments 38(3), 12–14.
Navarro (1978) "Reducing Feedback During the Hearing Aid Evaluation", Audiology & Hearing Educ. 4(6), 15.

(List continued on next page.)

*Primary Examiner*—Benjamin R. Fuller
*Attorney, Agent, or Firm*—Donald M. Sell; Walter N. Kirn; John H. Hornickel

[57] ABSTRACT

Disposably attached to the ear piece of a hearing aid, which includes any sound transmission device, is a user-disposable sleeve comprising soft polymeric retarded recovery foam that can be compressed to be freely insertable into a person's ear and allowed to recover to become wedged in the canal. Preferably, the sleeve is disposably attached to the ear piece by mating of screw threads on the sleeve and the ear piece. The ear piece may be a separate component from the hearing aid. The component is made either of rigid or flexible plastic and has connecting portions of various lengths depending on the depth of insertion of the sleeve into the canal. The sleeve may be of various lengths depending on the depth of insertion into the ear canal desired. The sleeve/ear piece assembly may also have a layer of sound transmitting scrim over its central opening to minimize penetration of the connecting portion past the end of the sleeve.

38 Claims, 5 Drawing Sheets

U.S. PATENT DOCUMENTS

| | | | |
|---|---|---|---|
| 3,529,102 | 9/1970 | Rosenstand. | |
| 3,539,032 | 11/1970 | Scanlon | 181/24 |
| 3,783,864 | 1/1974 | Moller | 128/152 |
| 3,882,848 | 5/1975 | Klar et al. | 122/22 |
| 3,895,627 | 7/1975 | Leight | 128/152 |
| 4,006,796 | 2/1977 | Coehorst | 181/130 |
| 4,253,452 | 3/1981 | Powers et al. | 128/152 |
| 4,375,016 | 2/1983 | Harada. | |
| 4,407,389 | 10/1983 | Johnson | 181/135 |
| 4,520,236 | 5/1985 | Gauthier. | |
| 4,532,649 | 7/1985 | Bellafiore | 381/69 |
| 4,552,137 | 11/1985 | Strauss | 128/152 |
| 4,607,720 | 8/1986 | Hardt | 181/135 |
| 4,677,679 | 6/1987 | Killion | 381/74 |
| 4,679,650 | 7/1987 | Moser et al. | 181/130 |
| 4,724,922 | 2/1988 | Kalayjian | 181/135 |

OTHER PUBLICATIONS

Frank (1980) "Attenuation Characteristics of Hearing Aid Earmolds", Ear and Hearing 1(3), 161–166.

Gerling et al., (1981) "A Modified Polymer Foam Earplug for the Hearing Aid Evaluation", Ear and Hearing 2(2), 82–87.

Smolak et al., (1987) "Disposable Foam Earmolds", Hearing Instruments 38(12) as reprinted.

"Enjoying the Sound of Life", Rionet ® Hearing Aid Brochure (Rion Co., Ltd. 1985).

3M "6300 Disposable Earplugs" and "Comply TM Custom Soft Earmold" Product Literature (3M Company 1987–1988).

Oticon "E42P" and "E43" Trade Literature (Oticon 1989).

EAR PIECE HAVING DISPOSABLE, COMPRESSIBLE POLYMERIC FOAM SLEEVE

This application is a continuation-in-part of U.S. patent application, Ser. No. 938,540, filed Dec. 5, 1986, U.S. Pat. No. 4,880,076.

BACKGROUND OF THE INVENTION

1. Field of the Invention

The invention relates to the ear piece of a hearing aid, namely the portion which is inserted into or otherwise covers the external ear canal The ear piece may be the hearing aid itself or a component thereof, for example, a canal hearing aid or an in-the-ear hearing aid; or an attachment, such as the end of a flexible sound tube of a behind-the-ear hearing aid or other sound transmission device. The ear piece often is molded to fit an individual's ear canal and sometimes has a compressible, resilient sleeve for enhanced comfort. Such a sleeve is often employed to permit one or a few ear pieces to fit nearly everyone, as do ear pieces of the invention.

2. Description of the Related Art

The problem of providing a hearing aid with an ear piece that can be continuously worn with comfort has long been a subject of research See, for example, U.S Pat. No. 1,753,817 (Aber). There, an impression of an individual's ear canal was used to mold an ear piece (there called an "audiphone cap"). Such a procedure is still in widespread use, even though time-consuming and expensive and requiring two visits to fit a person with a hearing aid. Moreover, the resulting ear piece is rigid, uncomfortable to wear, and prone to falling out of the ear canal.

U.K. Patent Application No. 2,091,063 (Blackstone) discloses the use of a layer of cushioning material, preferably one providing a high coefficient of friction, to seal a small gap between the external surface of a molded ear piece (called a "plastics molded component") and the internal surface of the ear canal, and to eliminate any whistling sound or echo effect. The molded ear piece approximates the shape of the external ear canal. Only a thin layer of the cushioning material is employed with the result that it does not provide a truly comfortable fit.

FIGS. 14–18 of U.S. Pat. No. 4,375,016 (Harada) show a layer of cushioning material in the form of a sleeve which fits over the distal end of the ear piece and is said to provide excellent fit without the necessity of using a custom molded construction. That sleeve is "formed from a compressible foam with characteristics as shown in U.S. Pat. No. Re. 29,487". The foam "can be compressed to a diameter less than that of the auditory canal. As the foam slowly attempts to return to its original configuration, it seals the auditory canal in a comfortable fashion as shown in FIGS. 17 and 18" (Col. 4, lines 41–56). However, the Harada patent does not indicate how the sleeve is prevented from remaining in the ear canal if the ear piece is either accidentally dislodged from the ear canal or simply pulled out. Rather than dealing with such matters, the Harada patent concentrates on the venting of excess sound pressure from the ear canal to the atmosphere.

The reissue patent (Gardner, Jr.) cited in the Harada patent does not concern hearing aids but describes an "earplug . . . composed of a resilient, plasticized polymeric foam containing a sufficiently high concentration of organic plasticizer to provide the foam with a rate of recovery from 60 percent compression to 40 percent compression in from 1 to 60 seconds and an equilibrium pressure at 40 percent compression thereof from 0.2 to 1.3 p.s.i." (claim 1). Cylindrical plugs of this material can be coaxially bored and employed as a covering over a tubular tip portion of a lightweight headphone set. However, like the Harada patent, Gardner does not indicate how the plug is prevented from remaining in the ear canal if the tubular tip portion is accidentally dislodged or simply pulled out Despite the approaches discussed above, none have been truly effective, particularly from the standpoint of providing an ear piece which is comfortable, retained during use, and readily removable when desired. Moreover, none have addressed a continuing problem in the hearing aid art, namely clogging of the sound tube by ear wax. Approximately half of professional repairs of hearing aids are either to remove ear wax or to repair damage caused by a user who tried to clean out the wax. That problem has been addressed in U.K. Patent Application GB No. 2,155,276A (Brander et al.); West German Offenlegungsschrift No. 2,818,273 (Sommer); and EPO Patent Application No. 85103722.6 (Laid open No. 0,159,571) (Moser et al.).

SUMMARY OF THE INVENTION

The present invention concerns the use of a user-disposable attachment with hearing aids, which for purposes of this invention includes any sound transmission device, such as ear phones, audio or transcription headsets, and the like.

The present invention provides, in one aspect, a user-disposable attachment to a hearing aid that should enable the user to keep its ear piece clean with only minimal; if any, risk of damage to the hearing aid Moreover, hearing aids utilizing this disposable sleeve enable the user to hear better, that is hear better quality sound. The novel user-disposable attachment comprises a sleeve which can be used with an in-the-ear hearing aid, a behind-the-ear hearing aid, a canal hearing aid, or other sound transmission device. The novel sleeve is:

(1) easy to use,
(2) easy to change,
(3) comfortable to wear due to its conformability and yet reliably stays in place,
(4) easy to manufacture, and
(5) conveniently fitted by an audiologist to almost any user or by the user himself.

Furthermore, by selecting from a set of sleeves of the invention, the audiologist will be able to provide each user with the best possible acoustical fit.

In another aspect, the invention provides an ear piece through which extends a sound tube. The ear piece, which can be integral with the hearing aid or a component thereof, has a connecting portion containing the sound tube extending from the ear piece and means thereon for disposably attaching a sleeve to the ear piece. The means may be either adjacent to the ear piece or distant from the ear piece depending upon the length of the connecting portion, the length of the sleeve, and the distance desired between the hearing aid and the location of the sleeve in the ear canal of the user.

In another aspect, the invention provides a hearing aid comprising the ear piece through which a sound tube extends plus the sleeve which is formed with a central longitudinal passage approximating the size of the sound tube. The sleeve comprises soft polymeric foam that has retarded recovery. That is, while being highly compressible, it has slow, substantially complete recovery, and can be compressed to be freely insertable into a user's external ear canal to become wedged in the canal when the foam is allowed to recover.

These retarded recovery attributes also are possessed by the foam sleeve of the hearing aid of FIGS. 14–18 of the above-cited Harada patent. Unlike that of the Harada patent, the sleeve of the present invention is user-disposable and the hearing aid of the invention includes means for disposably attaching the sleeve to the ear piece. When attached, said central longitudinal passage of the sleeve connects the sound tube to the user's ear. The attaching means should provide a Holding Value at least 1½ times the Pullout Value, each of which terms is defined hereinbelow. At substantially lower ratios of Holding Value to Pullout Value, there is a danger that the polymeric foam sleeve will be left in the person's ear canal if the ear piece were accidentally dislodged or otherwise pulled out.

The exterior surface of the novel sleeve preferably is substantially cylindrical, tapering slightly inwardly toward its distal end to enhance insertion into the user's ear canal. The sleeve may be formed either by molding or by cutting a section from a block. If the sleeve is molded, the exterior surface may possess a skin of higher density cell structure than that of the interior of the sleeve. This skin may minimize ear wax penetration of the foam; provide water resistance to the foam; and generally improve the cleanliness of the foam. Whether the sleeve is molded or cut from a block, protection from the connecting portion of the ear piece or a component thereof extending past the distal end of the sleeve may be provided by a sound transmitting scrim adhesively secured to the sleeve at its distal end or within the central longitudinal passage.

To remove the novel sleeve from the ear canal, the user may first wiggle the ear piece laterally to compress the foam of the sleeve, thus reducing the friction against the wall of the canal during removal.

In addition to its sound tube, the ear piece of a hearing aid contacting or covering the external ear canal usually is formed with one or more air vents, in which event the sleeve may be formed with air vents connecting one or more of those air vents to the inner reaches of the ear canal. When used with a hearing aid not contacting or covering the external ear canal, the air vents may open to the atmosphere. The air vents preferably are provided by flutes formed in the exterior surface of the polymeric foam of the novel sleeve, usually two, three or four flutes symmetrically positioned around the exterior surface When the exterior surface of the sleeve is substantially cylindrical, each flute preferably is semi-cylindrical, from 2 to 3 mm in breadth, and extends 1.0 to 1.5 mm beneath the substantially cylindrical surface.

To simplify changing sleeves by the user, the means for disposably attaching the sleeve preferably includes a duct over which the retarded recovery foam fits and to which the foam is firmly secured When the sleeve includes a duct, the central longitudinal passage of the sleeve is provided by the duct. The duct preferably comprises a moldable plastic that is flexible to allow it to conform to the user's external ear canal and to minimize any hazard of scratching or otherwise irritating the user's ear. The duct may be approximately the same length as the foam, with duct having a flange at its proximal end against which the foam is adhered. Alternatively, the duct may be elongated in comparison with the foam, with the foam adhesively secured to the flexible duct between its proximal and distal ends. Optionally, the elongated duct has a spiraled interior surface, a spiraled exterior surface, or both, to assist in its insertion into and withdrawal from the ear canal. When a sleeve with a flexible, elongated duct is used with an ear piece having either a rigid non-elongated connecting portion or a flexible, elongated connecting portion, the length of the combination permits the sleeve in the ear canal to be inserted a longer distance towards the tympanic membrane of the ear. This improves sound reception at the tympanic membrane.

Preferred materials from which a flexible plastic duct may be molded include a filled or unfilled semi-crystalline polymer such as plasticized poly(vinyl chloride) or crosslinked natural or synthetic elastomers such as natural rubber, chlorinated isoprene, silicone rubber, and block copolymers of styrene-dienes. The material of the duct preferably has a Shore durometer value between 40A and 40D. The foam may be secured to the duct by a layer of adhesive cement but preferably is molded onto the duct, thus serving as its own adhesive.

The means for disposable attachment of the duct and the ear piece can be formed with mating screw threads which preferably are self-aligning, e.g., tapered to guard against cross-threading. This makes it easy for the user to detach a used sleeve and securely attach a fresh sleeve. When the duct comprises a flexible plastic, the portion of the duct which is threaded preferably is more rigid. When the screw threads of the duct extend beyond the proximal end of the foam, they do not interfere with the compression of the foam. This is true whether the flange of the duct is at the proximal end of the sleeve or between the proximal and distal ends of the sleeve to provide an elongated duct with the screw threads more proximal to the ear piece than the foam.

Easy attachment and detachment can also be provided by forming the duct and the ear piece to provide bayonet or ball-and-socket attachments.

A preferred retarded recovery foam for the foam sleeve is that of the "Comply ™" earmolds available from 3M. These earmolds are resilient and recover slowly from compression to provide adequate time for insertion of a compressed earmold into the external ear canal before it recovers to fill the canal. These earmolds are formed from polyurethane foam which does not contain any plasticizer. The retarded recovery foam of the Gardner patent should also be useful but less preferred because of potential problems stemming from the tendency of plasticizers to migrate and volatilize.

Preferably the compressible, soft polymeric foam of the novel sleeves has a Retarded Recovery Value (as defined below) of at least 4 seconds and no more than 45 seconds, ideally from 15 to 35 seconds If the sleeve does not include a duct, it preferably is molded to form an impervious skin covering the walls of its central passage. Whether or not the walls of the central passage are provided by an impervious skin or a duct, those walls preferably are flared out at the distal end of the sleeve, thus minimizing the danger of blockage by ear wax.

BRIEF DESCRIPTION OF THE DRAWINGS

In the drawings, all figures of which are schematic.

EMBODIMENTS OF THE INVENTION

Figure 1:
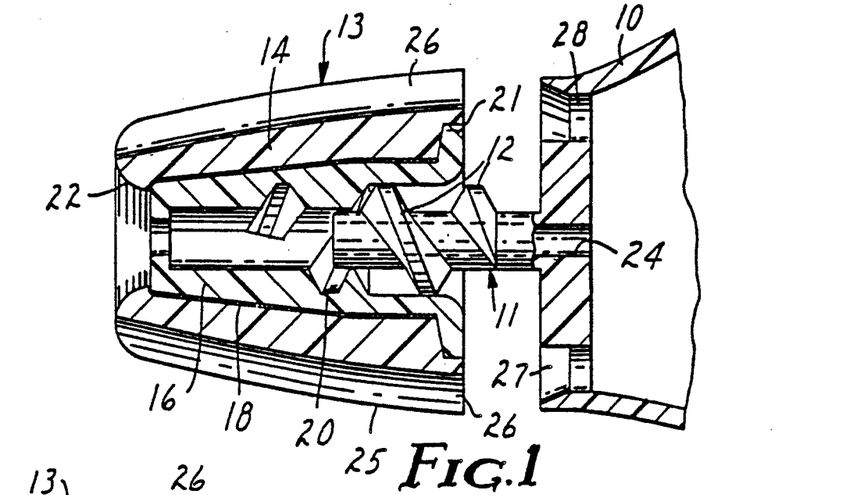
FIG. 1 is a longitudinal cross-section through a portion of a preferred hearing aid of the invention with its user disposable sleeve in position to be threaded onto its ear piece, parts thereof shown in elevation.
Figure 2:
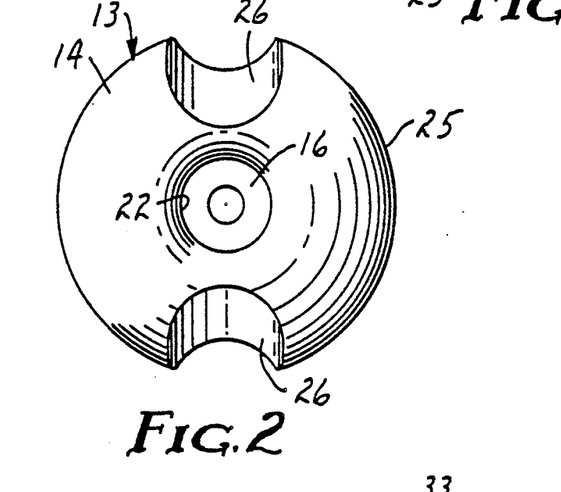
FIG. 2 is an end view of the hearing aid of FIG. 1.

Referring to FIGS. 1 and 2, the molded plastic casing 10 of a canal hearing aid has an ear piece 11, the external surface of which is formed with a male screw thread 12. A sleeve 13 consists of retarded recovery foam 14 and an internal, flexible, elongated plastic duct 16 formed with a longitudinal passage which provides a central passage for the sleeve 13. A substantially cylindrical layer of adhesive cement 18 secures the foam to the duct. The longitudinal passage through the duct 16 is formed with a female screw thread 20 which mates with the male screw thread 12 of the ear piece. When the sleeve 13 is threaded onto the ear piece 11, a flange 21 of its duct 16 comes to rest against the casing 10 of the hearing aid. At its distal end, the foam 14 has a flared opening 22 so that any wax from the user's ear which may accumulate on the foam is unlikely to block completely the portion of the sound tube that extends through the central passage of the sleeve 13 and connects to an internal passage 24 through the ear piece 11. When the foam is compressed to permit the assembly to be inserted into a person's ear canal and then allowed to recover to become seated, the compressive forces cannot substantially close its flared opening 22, because the foam extends only slightly beyond the distal end of the duct 16.

The external surface 25 of the foam 14 is substantially cylindrical except for two diametrically opposed flutes 26 which, when the foam is compressed by the user's ear canal, will communicate through an annular channel 27 to a series of cylindrical air vents 28 in the casing 10 (two of which are shown), the centers of which lie substantially in a circle concentric with axis of the male screw thread 12. The substantially cylindrical surface 25 of the foam 14 tapers inwardly toward its distal end to enhance insertion into the user's external ear canal.

Figure 3:
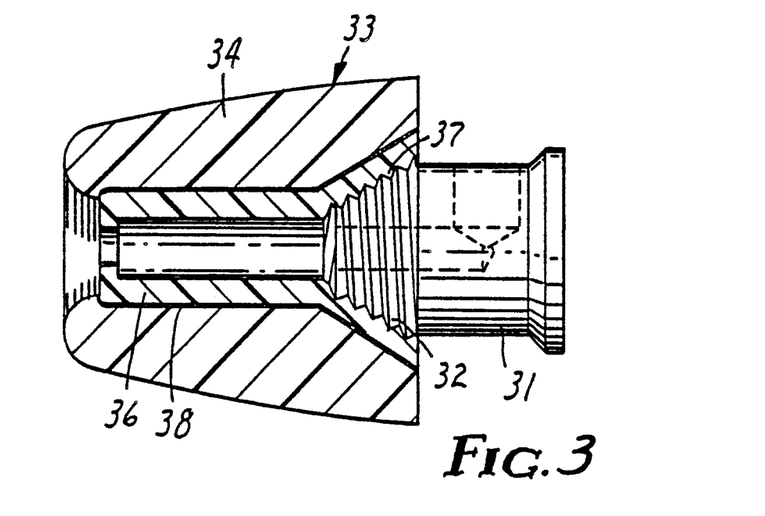
FIG. 3 is a longitudinal central cross-section through the ear piece and sleeve of another hearing aid of the invention, parts thereof shown in elevation.

Shown in FIG. 3 is an ear piece 31 of a behind-the-ear hearing aid, the distal end of which is formed with a self-aligning tapered male screw thread 32. Detachably secured to the ear piece 31 is a sleeve 33 that consists of retarded recovery foam 34, a flexible, elongated plastic duct 36, and a substantially cylindrical layer of adhesive cement 38 securing the foam to the duct. At the proximal end of the duct 36, its longitudinal passage is formed with a female screw thread 37 that mates with the male screw thread 32 of the ear piece 31.

Figure 4:
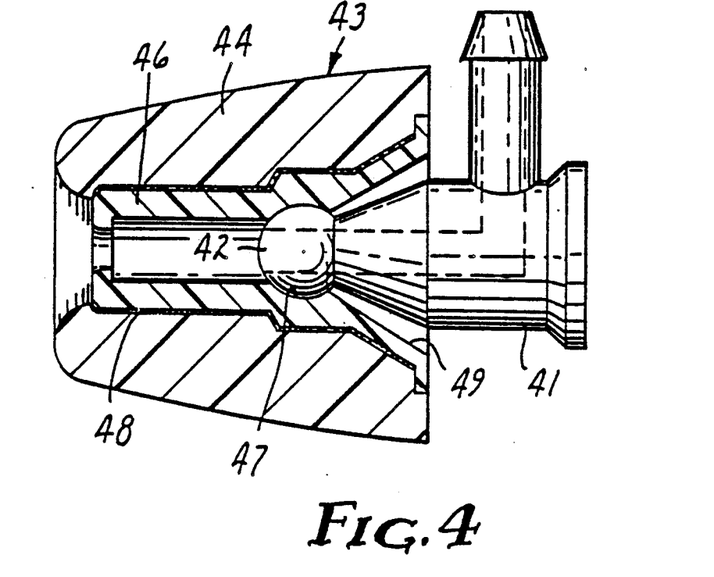
FIG. 4 is a longitudinal cross-section through the ear piece and sleeve of a third hearing aid of the invention, parts thereof shown in elevation.

Shown in FIG. 4 is an ear piece 41 of a behind-the-ear hearing aid, the distal end of which has a protuberance in the form of a ball 42. Detachably secured to the ear piece 41 is a sleeve 43 that consists of retarded recovery foam 44, a flexible, elongated plastic duct 46, and a substantially cylindrical layer of adhesive cement 48 securing the foam to the duct. The longitudinal passage through the duct 46 is formed with a socket 47 into which the ball 42 fits to permit the sleeve 43 to be readily attached or detached. The distal end 49 of the longitudinal passage of the duct 46 is conical to enhance attachment.

Figure 5:
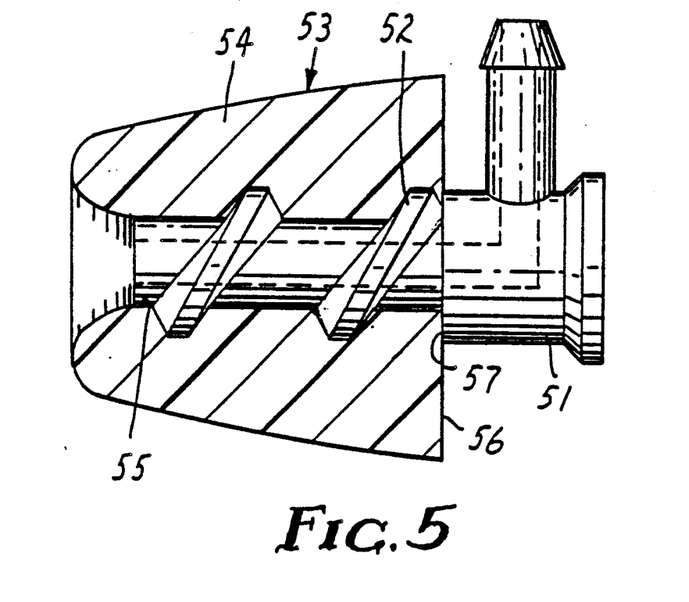
FIG. 5 is a longitudinal central cross-section through the ear piece and sleeve of a fourth hearing aid of the invention, parts thereof shown in elevation.

The behind-the-ear hearing aid of FIG. 5 has an ear piece 51, the external surface of the distal end of which is formed with a male screw thread 52, having a major diameter/minor diameter ratio of about 2. Disposably attached to the ear piece 51 is a sleeve 53 consisting of retarded recovery foam 54 formed with a cylindrical central passage 55. Because of the resilience of the foam, the sleeve has been self-threaded onto the male screw thread 52 of the ear piece 51 until its proximal surface 56 (which extends orthogonally to the axis of the passage 55) abuts the distal face 57 of the ear piece. By providing a high major diameter/minor diameter ratio, there should be no danger of leaving the sleeve in a user's ear upon withdrawing the ear piece from a wearer's ear, especially when the male screw thread is coarse and sharp.

Figure 6:
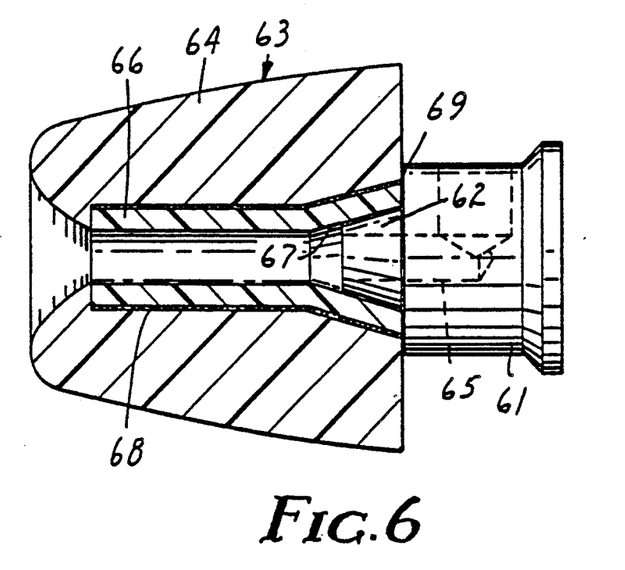
FIG. 6 is a longitudinal cross-section through the ear piece and sleeve of a fifth hearing aid of the invention, parts thereof shown in elevation.

The behind-the-ear hearing aid of FIG. 6 has an ear piece 61 which is formed with a tapered projection 62 having a central passage 65 to provide an outlet for its sound tube. Disposably attached to the ear piece 61 is a sleeve 63 consisting of retarded recovery foam 64, a flexible, elongated plastic duct 66, and a substantially cylindrical layer of adhesive cement 68 securing the foam to the duct. The proximal internal surface of the longitudinal passage 67 through the duct is tapered to mate with the projection 62. An annular layer of pressure-sensitive adhesive 69 on the proximal surface of the sleeve 63 contacts a smooth distal surface on the ear piece around its projection 62, thus releasably securing the sleeve to the ear piece.

A preferred pressure-sensitive adhesive layer 69 is "Scotch" A-60 acrylic systems No. 444 double-coated pressure-sensitive adhesive film tape from 3M.

Figure 7:
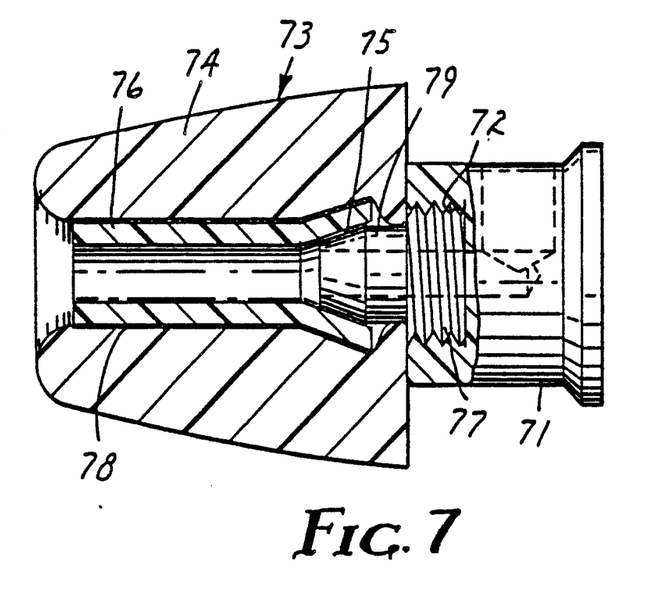
FIG. 7 is a longitudinal cross-section through the ear piece and sleeve of a sixth hearing aid of the invention, parts thereof shown in elevation.

The behind-the-ear hearing aid of FIG. 7 has an ear piece 71 which is formed with a female screw thread 72. Disposably attached to the ear piece 71 is a sleeve 73 consisting of retarded recovery foam 74, a flexible, elongated plastic duct 76, a layer of adhesive cement 78 securing the foam to the duct, and a rigid plastic adapter 79. The duct 76 and adapter 79 have been bonded together at 75 with a plastic solvent The proximal end of the adapter is formed with a male screw thread 77 which mates with the female screw thread 72 of the ear piece 71.

Figure 8:
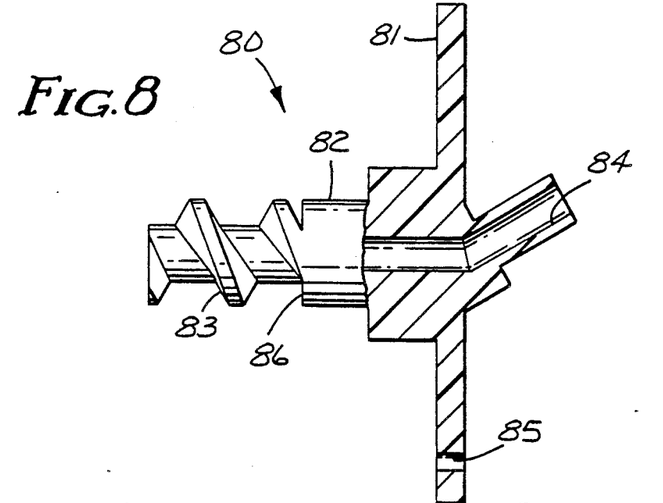
FIG. 8 is a longitudinal cross-section through a portion of an ear piece component of the invention showing the means for disposable attachment, parts thereof shown in elevation.

FIG. 8 shows the ear piece as a component to be used in attachment to a hearing aid (not shown). The component is an ear piece plate 80 having a plate flange 81 about a connecting portion 82, preferably cylindrical, of the same or similar non-elongated length as seen in the embodiment of the invention shown in FIG. 1. On the connecting portion 82 is a male screw thread 83 desirably having the same tapered geometry as that seen in FIG. 1 for male screw thread 12. Through connecting portion 82 is the sound tube 84 which has a size approximating that of the internal passage 24 of the ear piece 11 seen in FIG. 1. The material used for manufacture of the component plate 80 may be the same or similar material as that used for the manufacture of the duct 16 seen in FIG. 1, so long as the thread is slightly more rigid as preferred for the duct. Preferably, the component plate is made of the same or similar rigid plastic used in forming ear piece 11 seen in FIG. 1, using such materials as "Lexan 141" polycarbonate available from General Electric Co. or "Acrylic DR" acrylic polymer resin available from RTP Company of Winona, Minn.

The component plate 80 may be attached to the ear piece by adhesive bonding, solvent bonding, sonic welding, or other conventional securing methods used to secure two polymeric materials. The flange 81 is larger than the sound opening passageway of the ear piece, whether for a hearing aid, such as a canal aid, an in-the-ear hearing aid, a behind-the-ear hearing aid, or a headset After assembly to the ear piece, the excess portions of flange 81 are trimmed from the ear piece and air vents (shown as 85 for illustrative purposes) may be drilled through flange 81 for communication with vent(s) or trough(s) in the ear piece. Shoulder surface 86, against which the sleeve contacts, allows air venting between the sleeve and the flange 81.

The assembly of the hearing aid may be performed with versatility, with component plates 80 of various geometries, sizes, and means of disposable attachment being available for assembly with a hearing aid, either already in use and desired to be retrofitted or as a component for new manufacture. In the case of hearing aids for hard of hearing individuals, a custom molded canal or in-the-ear hearing aid shell having a opening smaller than the flange 81 may be formed and tested with a variety of means for disposably attaching the sleeve 13 seen in FIG. 1. The proper plate 80 may be selected without the expense and effort of forming a new molded hearing aid shell.

In the case of other hearing aids for sound transmission which are not custom molded to the contours of the ear, the interchangeability of the component plate 80 further aids the selection of the correct geometry, size and means of disposable attachment for best available comfort and sound transmission. The plate 80 to the ear piece may be removed for repair or replacement by severing the adhesive or solvent bond or sonic weld without harming the remainder of the ear piece, which is important when the repair must be made to a custom-made ear piece for the ear canal.

Figure 9:
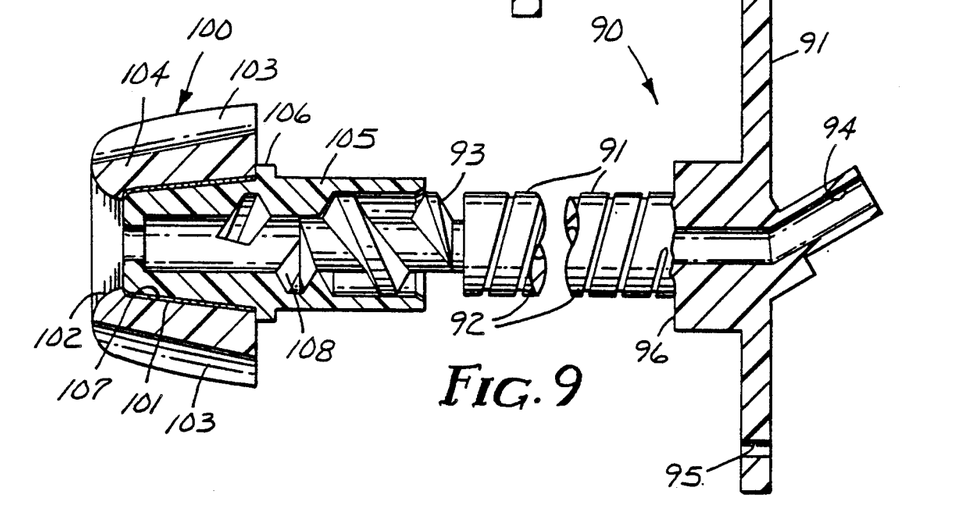
FIG. 9 is a longitudinal cross-section through a portion of an elongated ear piece component of the invention with its user disposable sleeve having an elongated duct in position to be threaded onto the ear piece component, parts thereof shown in elevation.

FIG. 9 shows the use of a component plate in a different size and geometry than that seen in FIG. 8 with a sleeve of a different geometry than that seen in FIG. 1. Component plate 90 has the same or similar flange 91 to flange 81 seen in FIG. 8 for securement to the ear piece with trimming the excess flange material and providing air vents 95. But the connecting portion 92 is elongated, of a desired length, compared to portion 82, on which male screw thread 93 is formed and through which sound tube 94 passes. Also, connecting portion, preferably cylindrical, has a spiraled recessed exterior surface 99 to facilitate bending of the elongated connecting portion 92. Optionally, the connecting portion 92 may be a separate cylinder, adhesive or solvent bonded or sonic welded to flange 91 at shoulder surface 96.

The materials used to manufacture the component plate 90 may be the same as that used in the manufacture of component plate 80. Desirably, the connecting portion 92 is made from a material which is flexible to permit some bending of the connecting portion 92, having sleeve 13 disposably attached thereon, around contours of the external ear canal, but retains its bended position once positioned in the external ear canal. Preferably, connecting portion 92 is made from injectable moldable "Santoprene Resin No. 201-NC" polyolefin-rubber based polymeric material (having a Durometer of 80 on the Shore A Scale) available from Monsanto Company and molded to flange 91 made from injection moldable materials used to make plate 80.

The sleeve 100 useful with component plate 90 may have foam of the same composition as foam 14, in size and geometry as the foam 14 of sleeve 13 seen in FIG. 1. Otherwise, geometries of foams 34, 44, 54, 64, and 74, seen in the prior FIGS. 1, 3, 5, 6, 7, respectively, may be used depending on the geometry of the duct and means for disposable attachment on the duct and the connecting portion 92. As seen in FIG. 9, the foam 14 may have the same size but a different geometry caused by truncating its length on the sleeve 100. Flutes 103 and the flared opening 102 are also desirable whichever foam 104 geometry is selected.

Sleeve 100 desirably has a different duct 105, elongated relative to foam 104, for disposable attachment with the ear piece plate component 90. The duct 105 has an aligning flange 106 between its proximal and distal ends of the duct 105 and sleeve 100 so that the adhesive 101 may hold the foam 104 at its proximal end at flange 106 of duct 105. Duct 105 has a central longitudinal passage 107 having a female screw thread 108 to mate with male screw thread 93 on plate component 90. Desirably, the threads 93 and 108 are self-aligning and tapered in the same manner and for the same reason as that described for threads 12 and 20 in FIG. 1.

Duct 105 is made of a flexible but sturdy material capable of maintaining attachment with plate component plate 90. Desirably, duct 105 is made of the same material as the duct 16 as seen in FIG. 1 to provide flexible insertion into the external ear canal and maintain position once in the external ear canal.

Depending on the depth of insertion desired into the ear canal, the sleeve 100 may be used with component plate 80 or component plate 90. Use of the component plate 90 having elongated connecting portion, preferably cylindrical, 92 with elongated duct 95 permits the placement of the foam 104 deep into the external ear canal toward the tympanic membrane.

Figure 10:
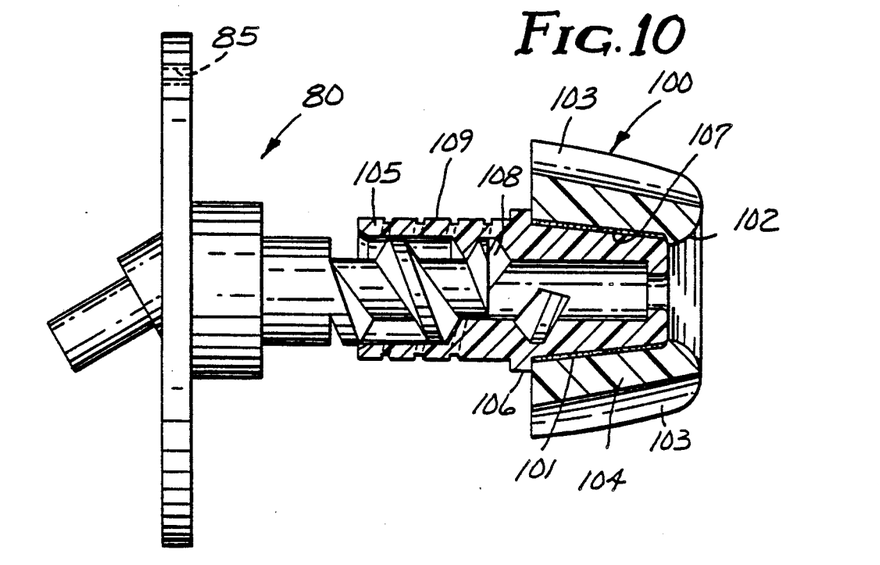
FIG. 10 is a longitudinal cross-section through a portion of an ear piece component of the invention with its user disposable sleeve having an elongated duct with a spiraled exterior surface positioned to be threaded onto the ear piece component, parts thereof shown in elevation.

FIG. 10 illustrates the use of sleeve 100 with plate 80, with the optional feature of providing on the surface of the duct 105 between aligning flange 106 and the sleeve's proximal end, a spiraled recessed surface 109 on the exterior of the connecting portion 82 to further assist in the deep insertion and placement of the sleeve 100 on plate 80 into the ear canal. Desirably as seen in FIG. 10, the direction of the spiraled recesses is the opposite to the direction of the threads 93 and 108 to aid in a twisting insertion into the ear canal without detaching the sleeve 100 from the plate 80 and in removal of the sleeve from the ear canal. The spiraled recessed surface 109 also provides a flexible retention of the position of the sleeve in the ear canal. Alternatively, the spiraled recessed surface 109 may be on the passage 107. It is possible to have spiraled recessed surfaces, desirably in biasing directions, on the exterior and interior surfaces of duct 105.

Figures 11, 12:
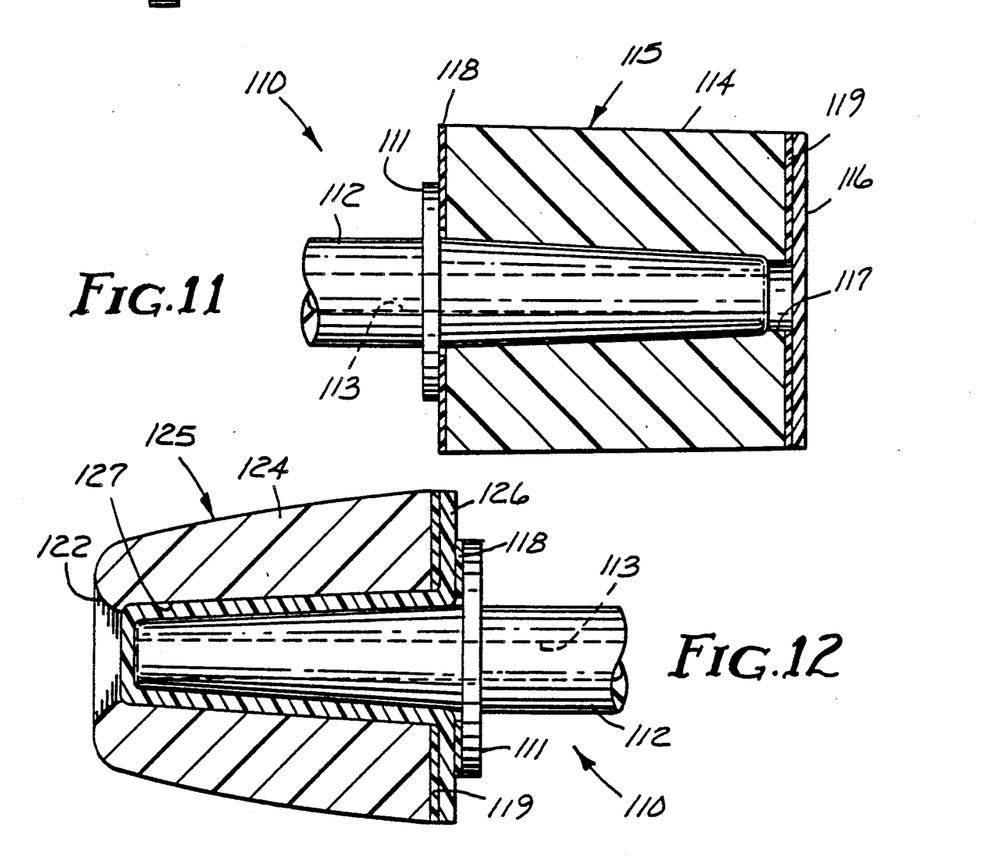
FIG. 11 is a longitudinal cross-section through a second sleeve of the invention disposably attached to another ear piece component of the invention, shown in elevation.
FIG. 12 is a longitudinal cross-section through a second embodiment of the second sleeve of the invention.

FIG. 11 shows another embodiment of the sleeve less expensively produced for limited insertion into the rim of the ear canal. Ear piece 110 may be integral with a sound tube or other lumen creating passageway to a remote headset or other remote hearing aid or other sound transmission device. Alternatively, ear piece 110 may be a component such as those components 80 and 90 seen in FIGS. 8 and 9. Ear piece 110 has a flange 111 against which sleeve 115 is disposably attached. For that reason, even if flange 111 also is adhered to an ear piece, no trimming of excess material is done. The flange 111 is wide enough to permit disposable attachment of sleeve 115 to it but not so large as to prevent venting to occur using one or more flutes on the sleeve (not shown).

Ear piece 110 also has smooth surface projection 112, desirably distally tapering and otherwise similar to projection 62 seen in FIG. 6 through which sound passage 113 extends. While projection 112 may be made of the same or similar material as that used to make components 80 and 90, desirably, projection is made from the same or similar flexible material as used to make ducts 16 and 105 to provide flexibility where projection 112 is inside sleeve 115 and otherwise outside to the remainder of the ear piece 110.

Sleeve 115 has foam 114 of the same material as used in foam 54 seen in FIG. 5. The foam 114 has a central longitudinal passage 117 to permit sound communication and insertion of the smooth surface projection 112 into foam 114. Foam 114 directly contacts the smooth surface of projection 112 in the absence of a duct for receiving the projection 112.

In the absence of mating screw thread such as thread 52 seen on ear piece 51 in FIG. 5, sleeve 115 also has a layer of adhesive 118 to disposably attach in abutment the proximal end of the foam 114 to the flange 111 of the ear piece 110. Prior to abutting flange 111 and otherwise during storage prior to use, adhesive layer 118 is protected by contact with a silicone release liner (not shown).

Desirably, the distal end of sleeve 115 has a sound transmitting scrim 116 thereto to minimize any possible penetration of the projection 112 past the distal end of the foam 114 during insertion of the sleeve 115 into the ear canal. The scrim 116 is secured over the central longitudinal passage 117 and secured by adhesive 119. The scrim may be any thin material which transmits sound but has sufficient strength to resist puncture by projection 112. Preferably, a urethane nonwoven material having a thickness of about 0.18 mm is used. That urethane material is commercially available from either Pellon Corporation of Chelmsford, Mass. under the brand "Bondina TM" spun bond urethane (product #M11329) or from Kanebo Ltd. of Japan distributed by Chori America of Los Angeles under the brand "Kanebo TM" urethane spun bond (products ES-254, EH-501 or EH-75 having 25, 50, and 75 grams per square meter basis weight, respectively).

The adhesive 119 may be any adhesive which aggressively secures the urethane nonwoven scrim 116 to foam 114. Acceptable adhesives include urethane bonding adhesives which are dermatologically acceptable and approved for use by governmental authorities. Such adhesives are commercially available from Ashland Chemical (Products 1085-Z-45; 1113-A5-40; 1810-Z-52; 1880-Z-46; 1920-Z-52; 1930-TH-45), Monsanto Company (Products GMS-737; GMS-788; GME-2333; GME-2397; GME-2484; and GME-3011), and National Starch and Chemical (Products 80-1054; 80-1070; 80-1194; 80-2434; 36-6172; 72-9573; and 72-9574).

The adhesive layer 118 on the proximal end of the sleeve 115 needs to be aggressive yet highly cohesive in its disposable attachment of the sleeve 115 to ear piece 110. The adhesive can be any of the adhesives commercially available and described for adhesive 119. Desirably, the adhesive is an acrylate based adhesive described in U.S. patent application Ser. No. 106,414 assigned to the same assignee as this application, the disclosure of which is hereby incorporated by reference as if fully rewritten herein.

The method of preparing the sleeve 115 involves applying a coating of adhesive 119 on a surface of a block of foam material, roll laminating a tape of adhesive 118 on a release liner to the opposite surface of the block of foam material, rule die punching the longitudinal passage 117, laminating the scrim 116 to the adhesive 119, compressing the foam material and die punching the foam 114 from the block of foam material. If adhesive 119 is applied in solution, the adhesive is air dried and then heat dried at a temperature less than the melting point of the foam 114 for a sufficient time to dry the adhesive 118. If the projection 112 is to be inserted into sleeve 115 without storage delay, there is no need for a protective release liner. Otherwise, the release liner typically made with a silicone containing release surface remains contacted against the adhesive 118 until disposable attachment of the sleeve 115 on the ear piece 110 is desired.

It is important to cut foam 114 from the block of foam material in a precise manner to avoid misshapen sleeves. The compression of the foam material during cutting must be perpendicular to the surface of the foam material in order to yield the cylindrical shaped sleeve 115 seen in FIG. 11.

Another method of forming sleeve 115 is to mold the foam 114 into a conically shaped plug and then slice in a parallel manner opposite ends of the plug to yield a frustroconical shape. Other steps of the method follow as stated above to apply the adhesives and scrim and rule die punch the longitudinal passage.

FIG. 12 illustrates another structure for sleeve 125. In this embodiment, the scrim 126 is adhesively secured to the proximal end of the molded foam 124 and has sufficient material to extend into as much of longitudinal passage 127 as projection 112 is intended to be inserted. This embodiment permits the use of a flared distal end 122 at longitudinal passage 127 in foam 124 in order to provide the same function as flared opening 22 in FIG. 1.

The method of manufacture for this embodiment of FIG. 12 is the name as stated above for sleeve 115 except that the adhesive 119 is applied to the proximal end and the scrim 126 is of such a size that it can be inserted into the passage 127 prior to applying the adhesive layer 118.

Holding Value

Drilled in aluminum block 1.6 cm in thickness are a number of holes, each 0.344 inch (8.74 mm) in diameter. After coating a hole with adhesive cement, a sleeve to be tested is compressed to permit insertion and then allowed to expand against the adhesive cement. After standing in a room temperature environment (23° C., 48% relative humidity) for at least one day to allow the adhesive cement to cure, the jaw of a tensile tester ("Instron" Model 1122) is clamped either onto a protruding duct of the sleeve or, if there is no duct, onto a portion of an ear piece onto which the sleeve has been fitted. The assembly is then warmed to 37° C., held at that temperature for 3 minutes, and then immediately tested in the room temperature environment by measuring the axial force required to pull the duct or ear piece out of the foam at a rate of about 25.4 cm/min.

Pullout Value

This test is carried out in the same way except as follows: The holes in the aluminum block are reamed (but not polished) to a roughness of 32 microinches (0.8 micrometers) peak-to-valley, and no adhesive is applied to the holes. After standing for at least three minutes, the tensile tester measures the axial force required to pull the sleeve out of the hole.

Retarded Recovery Value

A 8.0-mm cube is cut from the foam and then held for 24 hours at 23° C., 48% relative humidity and tested under those conditions. While standing on an aluminum plate, it is compressed to 1.6 mm using an aluminum piston 19 mm in diameter and immediately released. The time required for it to recover to a height of 6.4 mm is the Retarded Recovery Value of the foam.

EXAMPLE 1

A number of sleeves were made as illustrated in FIG. 7 using unplasticized polyurethane foam identical to that used in the "Attenutech" 6300 earplugs now used in "Comply TM" earmolds available from 3M. The foam had a Retarded Recovery Value of 27 seconds. When tested according to ANSI Specifications S3.19-1974, it provided a noise reduction rating of 29 dB. The flexible plastic duct 76 was molded of plasticized poly(vinyl chloride), and the foam was adhered to the duct using plastic adhesive No. 4475 from 3M. Its rigid plastic adapter 79 was polycarbonate. Significant dimensions were:

| Foam 74 | |
|---|---|
| maximum outer diameter | 12.7 mm |
| length | 15.9 mm |
| Duct 76 | |
| length | 12.7 mm |
| outer diameter | 3.1 mm |
| inner diameter | 1.9 mm |

Using a die punch, the foam of each of the sleeves had been formed with a central passage 3.2 mm in diameter while sometimes simultaneously forming 2, 3 or 4 symmetrically arranged flutes, 3 3/16 inch (4.80) in diameter and centered on the maximum circumference of the foam.

A set of four such sleeves including one with no flutes should permit an audiologist to fit 80-90% of potential users while also affording whatever level of venting is desired.

A number of persons have worn such sleeves with their hearing aids, and a majority of them reported enhanced comfort and improved sound quality.

EXAMPLE 2

A number of sleeves were made substantially as illustrated in FIG. 5 using the same foam as was used in Example 1. Using a die punch, the foam was formed with a central passage 2.4 mm in diameter, and flutes were simultaneously formed in some of the sleeves as in Example 1. Each sleeve was self-threaded onto the male screw thread 52 of the ear piece 51 which had been formed of a rigid plastic ("Ultem" from G.E.) as follows:

| | |
|---|---|
| major diameter of thread | 4.6 mm |
| minor diameter of thread | 2.8 mm |
| pitch of thread | 0.55 thread/mm |
| width at crown | 0.25 mm |
| thread profile | |
| of leading (distal) face | 105° |
| of trailing (proximal) face | 95° |

EXAMPLE 3

A number of sleeves were made as illustrated in FIG. 6, except that, for purposes of testing, the duct 66 extended beyond the proximal end of the foam 64. The foam and duct were made from the same materials as were used in Example 1.

| | Testing | |
|---|---|---|
| | Pullout Value (gm force) | Holding Value (gm force) |
| Sleeves of Example 2 | | |
| No flutes | 240 | 2033 |
| 2 flutes | 190 | 1843 |
| 3 flutes | 145 | 1585 |
| 4 flutes | 110 | 1442 |
| Sleeves of Example 3 | | |
| No flutes | 279 | 623 |
| 2 flutes | 176 | NT |
| 3 flutes | 131 | NT |
| 4 flutes | 105 | 189 |

NT = not tested

EXAMPLE 4

Samples of component plate 80 were made by injection molding the "Acrylic DR" acrylic resin from RTP Company in a water-cooled die having a cavity shaped in the form of plate 80 at about 27° C. in an Arburg Injection Molding Machine. The acrylic resin pellets were dried for about 4 hours at about 66° C. to drive off surface moisture. The pellets were then melted at about 233° C. and injected under hydraulic pressure into the water-cooled die with a line pressure of about 600 pounds/inch$^2$ using a 2.5 cm diameter cylinder compressing down to 0.31 cm diameter. After about 15 seconds the molded plate 80 was removed from the die cavity.

The component plates had the following dimensions:
Major diameter of thread: 3.1 mm
Minor diameter of thread: 2.1 mm Pitch of Thread: 0.39 thread/mm
Width of Crown: 0.30 mm
Thread Profile of leading (distal) face: 120°
Thread Profile of trailing (proximal) face: 120°

The component plates 80 were oriented at the appropriate angle to the shell of the hearing aid as that seen in FIG. 1 and then bonded to the openings of shells of hearing aids made of polymethyl methacrylate by applying a modified methyl methacrylate monomer in solution, Product A-8001 available from Esschem and distributed by Electone of Winter Park, Fl. and maintaining hand pressured contact for about 10 minutes at room temperature in open air to drive off the solvent. After 5 more minutes, the excess flange 81 was trimmed and polished, and the vent 85 was drilled into venting in the shell of the hearing aid.

EXAMPLE 5

Elongated plate 90 is made of a flange injection molded in a modified cavity to that used in Example 4 but otherwise using the procedures of Example 4. That flange is placed into a die cavity for forming the connecting portion where the connecting portion is elongated to 24 mm in length. The connecting portion is injection molded using a 30 Ton Newberry Injection Molding Machine in the die water cooled at about 27° C. having a cavity to form a spiraled recessed surface 109 having a recess of 0.4 mm in a spiral of 0.3 spirals/mm. The connecting portion is formed of "Santoprene" resin melted at about 173° C. and injected at a line pressure of 500 pounds/in$^2$ into the die cavity. After about 15 seconds, the plate of an acrylic flange and a Santoprene connecting portion is removed.

EXAMPLE 6

The sleeve 100 seen in FIGS. 9 or 10 is made like sleeve 13 now is made, by molding the foam 104 from the unplasticized urethane material used in Examples 1-3 molded here in a length of 11.11 mm, an outer diameter of 12.7 mm, and a central passage diameter of 3.6 mm. The duct 105 is injection molded using a 30 Ton Newberry Injection Molding Machine in a water-cooled die at about 27° C. having a cavity matching the shape of duct 105 having a length of about 24.0 mm without or with spiraled recessed surface 109 of the dimensions used in Example 5 using "Santoprene" resin melted at about 173° C. and injected at a line pressure of 500 pounds/in$^2$ into the die cavity. After the duct 105 is removed, it is coated with "Chemlok" 459 urethane bonding adhesive available from Lord Corporation of Erie, Pa. The adhesive is allowed to air dry for about 15 minutes. A second coat is applied and allowed to dry for about one hour. Before assembly into foam 104, the adhesive coated duct 105 is dipped in xylene, with excess xylene shaken off, to lubricate the adhesive surface. Foam 104 is then pressed on to duct 105 through central passage 107. The adhesive bond is cured at about 115° C. for about 15 minutes at atmospheric pressures.

After cooling, the sleeve 100 is screwed on thread 83 of plate 80 to make the assembly shown in FIG. 10 or screwed on thread 93 of plate 90 to make the assembly shown in FIG. 9.

EXAMPLE 7

The sleeve 115 seen in FIG. 11 is made by coating about 0.05 mm of "1930-TH-45" adhesive available from Ashland Chemical Company on a block of foam material made of the same foam material as used in Examples 1-3, and 6, approximately 16 mm thick. The opposite surface of the block of foam material is roll laminated with a layer of adhesive made according to U.S. patent application Ser. No. 106,414, Example 2 of about 0.25 mm thick on a silicone containing release liner in the form of a tape. The adhesive enveloped foam block is then rule die punched using a 3.175 mm diameter punch at about 110 lbs/inch$^2$ to form the central longitudinal passage. While the block is maintained in static position, a layer of "Bondina" spun bond urethane about 0.17 mm thick is laminated to the adhesive. The foam block sandwich of scrim, adhesive, foam, adhesive and release liner is compressed at room temperature at a pressure of about 2 lbs/inch$^2$ and die punched with a cylindrical punch of approximately 12.7 mm outside diameter at a pressure of about 110 lbs/inch$^2$ before the foam can recover from compression. The punched cylindrical sleeve is formed and upon removal of the release liner, the sleeve is disposably attached to the flange 111 of projection 112.

While a variety of embodiments and examples have been described, the invention is not to be limited thereto. For an understanding of the scope of the invention, reference is made to the following claims.

What is claimed is:

1. An ear piece component for use with a user-disposable sleeve, having a duct and soft polymeric foam firmly secured to the duct, to facilitate transmission of sound to an ear canal of a user, said ear piece component comprising:
    a connecting portion having (i) distal and proximal ends and an exterior surface between said distal and proximal ends, (ii) a sound tube extending through said connecting portion between said distal and proximal ends, and (iii) means on said exterior surface for disposably attaching the duct of the sleeve to said connecting portion, and
    a flange portion secured to said proximal end.

2. An ear piece component according to claim 1, wherein said means for disposably attaching comprises a screw thread mating with the user-disposable sleeve.

3. An ear piece component according to claim 2, wherein said screw thread comprises a male thread.

4. An ear piece component according to claim 3, wherein said male screw thread is tapered.

5. An ear piece component according to claim 1, wherein said means for disposably attaching comprises a projection on said exterior surface of said connecting portion for mating with the user-disposable sleeve.

6. An ear piece component according to claim 5, wherein said projection comprises a distal end comprising a ball-shaped protuberance.

7. An ear piece component according to claim 5, wherein said projection is tapered and has a smooth surface for receiving an adhesive layer to disposably attach said connecting portion to the sleeve.

8. An ear piece component according to claim 1, wherein said connecting portion is cylindrical.

9. An ear piece component according to claim 1, wherein said connecting portion is flexible and elongated in length.

10. An ear piece component according to claim 9, wherein said means for disposably attaching comprises a male screw thread mating with the user-disposable sleeve.

11. An ear piece component according to claim 10, wherein said connecting portion exterior surface is spiraled and recessed.

12. An assembly for transmitting sound to an ear canal of a user, comprising:
(a) a user-disposable sleeve comprising a duct and soft polymeric foam firmly secured to said duct,
said sleeve formed with distal and proximal ends and a central longitudinal passage between said distal and proximal ends, and
(b) an ear piece component comprising a connecting portion having (i) distal and proximal ends and an exterior surface between said distal and proximal ends, (ii) a sound tube extending through said connecting portion between said distal and proximal ends, and (iii) means on said exterior surface for disposably attaching said duct of said sleeve to said connecting portion in said central longitudinal passage, and
a flange portion attached to said proximal end.

13. An assembly according to claim 12, wherein said foam is highly compressible, has a slow, substantially complete recovery, and can be compressed to be freely insertable into an ear canal of the user and to become wedged in the canal when the foam is allowed to recover.

14. An assembly according to claim 13, wherein said connecting portion is flexible and elongated,
wherein said means for disposably attaching comprises a male screw thread, and
wherein said sleeve is flexible and further comprises means for mating with said male screw thread.

15. An assembly according to claim 14, wherein said flexible elongated connecting portion exterior surface is spiraled and recessed.

16. An assembly according to claim 13, wherein said duct comprises a moldable flexible plastic and has an aligning flange extending therefrom between the proximal and distal ends of said sleeve, and
wherein said foam is firmly secured to said duct between said aligning flange and the distal end of said sleeve.

17. An assembly according to claim 16, wherein said flexible duct is elongated and has at least one spiraled recessed surface.

18. An assembly according to claim 13, wherein said foam has an exterior surface and at least one flute for venting the ear of the user.

19. An assembly according to claim 12, wherein said means for disposably attaching comprises a projection on said exterior surface of said connecting portion for mating with the user-disposable sleeve.

20. An assembly according to claim 19, wherein said projection comprises a distal end insertable into said central longitudinal passage of said sleeve and said distal end comprises a ball-shaped protuberance.

21. An assembly according to claim 19, wherein said projection is tapered and has a smooth surface for receiving an adhesive layer to disposably attach to said sleeve.

22. A user-disposable sleeve freely insertable into an ear canal of a user for facilitating transmission of sound to the ear of the user, comprising:
(a) a soft, retarded recovery polymeric foam having proximal and distal ends and a central longitudinal passage therethrough, and
(b) a moldable flexible plastic duct having proximal and distal ends, an exterior surface, and an aligning flange extending from said exterior surface between said proximal and distal ends,
said foam firmly secured to said duct between said aligning flange and said distal end of said duct.

23. A user-disposable sleeve according to claim 22, wherein said duct is elongated.

24. A user-disposable sleeve according to claim 23, wherein said duct has at least one spiraled recessed surface.

25. A user-disposable sleeve for limited insertion into the rim of an ear canal of a user for facilitating a transmission of sound to the ear of the user, comprising:
(a) a soft polymeric foam having proximal and distal ends, a central longitudinal passage therethrough,
said foam having a slow, substantially complete recovery and capable of being compressed to be insertable into the rim of the ear canal of the user and to become wedged into the ear canal when said foam is allowed to recover; and
(b) a sound transmitting, puncture resistant scrim covering said central longitudinal passage.

26. A user-disposable sleeve, according to claim 25, further comprising a layer of adhesive on said proximal end of said sleeve.

27. A user-disposable sleeve, according to claim 26, further comprising a layer of adhesive between the distal end of said sleeve and said scrim.

28. A user-disposable sleeve, according to claim 26, wherein said scrim resides between said proximal end of said sleeve and said adhesive layer, said sleeve further comprising a second layer of adhesive between the proximal end of said sleeve and said scrim, and wherein said scrim extends into said central longitudinal passage from said proximal end of said sleeve.

29. A user-disposable sleeve, according to claim 25, wherein said foam has an exterior surface and has at least one flute on said exterior surface for venting the ear canal of the user.

30. A user-disposable sleeve, according to claim 29, wherein said foam is a polyurethane foam which is free from plasticizer.

31. A user-disposable sleeve, according to claim 30, wherein said polyurethane foam has a Retarded Recovery value which is no less than 4 seconds and no more than 45 seconds.

32. An assembly for transmitting sound to the ear canal of a user, comprising:
(a) a user-disposable sleeve comprising a soft, retarded recovery polymeric foam, said sleeve formed with distal and proximal ends, a central longitudinal passage between said distal and proximal ends, and a sound transmitting scrim covering said central longitudinal passage; and
(b) a connecting portion having distal and proximal ends and an exterior surface between said distal and proximal ends, a sound tube extending through said connecting portion between said distal and proximal ends communicating with said central longitudinal passage, said connecting portion having an abutment flange on said exterior surface for disposably attaching said proximal end of said sleeve to said distal end of said connecting portion.

33. An assembly according to claim 32, further comprising a layer of adhesive between said abutment flange and said proximal end of said sleeve for such disposable attachment of said sleeve to said connecting portion.

34. An assembly according to claim 33, wherein said scrim resides between said proximal end of said sleeve and said adhesive layer, said sleeve further comprising a second layer of adhesive between said proximal end of said sleeve and said scrim, and wherein said scrim extends into said central longitudinal passage from said proximal end of said sleeve.

35. An assembly according to claim 32, further comprising a layer of adhesive between the distal end of said sleeve and said scrim.

36. An assembly according to claim 32, wherein said foam has an exterior surface and at least one flute on said exterior surface for venting the ear canal of the user.

37. An assembly according to claim 36, wherein said polymeric foam is a polyurethane foam which is free from plasticizer.

38. An assembly according to claim 37, wherein said polymeric foam has a Retarded Recovery Value which is no less than 4 seconds and no more than 45 seconds.

* * * * *